United States Patent [19]
Beers

[11] Patent Number: 5,446,544
[45] Date of Patent: Aug. 29, 1995

[54] TURBIDIMETER

[75] Inventor: Howard L. Beers, North Fort Myers, Fla.

[73] Assignee: HF Scientific, Inc., Fort Myers, Fla.

[21] Appl. No.: 8,574

[22] Filed: Jan. 22, 1993

[51] Int. Cl.⁶ .......................................... G01N 21/53
[52] U.S. Cl. .................................... 356/339; 356/73; 356/435
[58] Field of Search ................. 356/338, 339, 435, 73; 359/512; 357/739

[56] References Cited

U.S. PATENT DOCUMENTS

| | | | |
|---|---|---|---|
| 3,177,760 | 4/1965 | Albert | 356/339 |
| 3,800,147 | 3/1974 | Shea | 356/442 |
| 3,826,574 | 7/1974 | Brown | 356/339 |
| 3,918,817 | 11/1975 | Posgate | 356/246 |
| 4,343,552 | 8/1982 | Blades | 356/339 |
| 4,637,730 | 1/1987 | Ponstingl et al. | 356/435 |
| 5,123,739 | 6/1992 | Takenouchi et al. | 356/319 |

Primary Examiner—Richard A. Rosenberger
Attorney, Agent, or Firm—William E. Noonan

[57] ABSTRACT

A turbidimeter including a sensor apparatus that has a housing with first and second receptacles. An incident light beam is established within the housing by a light source module that is releasably engaged with the first receptacle. A test liquid holder is removably engaged with the first receptacle. A test liquid holder is removably received by the second receptacle for positioning a liquid to be tested in the path of the incident beam. A photodetector or analogous instrument is provided at an angle to the incident light beam for sensing light scattered by the test liquid. An analyzer apparatus includes appropriate circuitry that is responsive to the photodetector for determining the turbidity of the test liquid. The turbidity is then displayed in both graphic and instantaneous alphanumeric form.

16 Claims, 7 Drawing Sheets

TURBIDIMETER

FIELD OF THE INVENTION

This invention relates to a turbidimeter and, more particularly, to an apparatus that is used in a water filtration system to monitor both the turbidity of the filtered water and the light transmittance of the filter backwash.

BACKGROUND OF THE INVENTION

Governmental regulations typically require that public water supplies be tested and monitored for turbidity. Generally speaking, turbidity is the measure of small particulate matter suspended in a liquid, which matter causes light passing through the liquid to be scattered or absorbed. Conventional nephelometric turbidimeters operate by projecting a light beam through a water sample. A detector is placed at an angle to the light beam such that it measures the scattering or reflecting of light caused by the particulate matter in the liquid.

A number of problems are encountered by known turbidimeters, particularly those that are used in the field, such as at water filtration plants. For example, most turbidimeters employ an encased light source which periodically fails. Changing the light source can be an aggravating and time consuming procedure, which requires opening the housing of the turbidimeter to access the light source. This can subject the electronics of the apparatus to moisture and contamination. Additionally, when the light source is changed the turbidimeter must be recalibrated. This is very often a messy procedure which involves the handling and mixing of carcinogenic substances such as Formanzin.

A further problem experienced by conventional turbidimeters is their tendency to exhibit erroneous readings, particularly in humid environments. Typically, the water sample is introduced into the turbidimeter in a glass cuvette. When a cuvette containing relatively cold water is exposed for cleaning, calibration etc., the humid outside air tends to cause condensation to form on the cuvette. This often results in erroneously high measurements.

Monitoring filter backwash also presents difficulties in the field. Filter backwash refers to the percentage of light transmitted through water backwashed through the filter. A filtration system must be backwashed at frequent intervals to clean the filter when it becomes clogged. Measuring turbidity and backwash are mutually exclusive tasks since turbidity has no meaning during backwash. Accordingly, in most cases, the backwash monitor includes its own electronics, which are entirely separate from the turbidimeter. As a result, the water filtration system requires a complex array of sensors and analyzing electronics. Presently, no compact and conveniently usable monitoring system is known for selectively measuring turbidity and backwash.

The indicator displays used by most turbidimeters are likewise problematic, particularly for providing an accurate history of the turbidity of the water supply. Known apparatuses often employ a strip chart recorder that records the turbidity measured at predetermined time intervals. However, it is possible that the recorded turbidity may be a spurious high or low reading and may not accurately reflect the average turbidity during the time period in question. As a result, the recorded history may not be entirely accurate.

SUMMARY OF THE INVENTION

It is therefore an object of the present invention to provide an improved turbidimeter for effectively monitoring turbidity and filter backwash transmittance in a water filtration system.

It is a further object of this invention to provide a turbidimeter that is especially effective for use in the field.

It is a further object of this invention to provide a turbidimeter employing a modular light source that is replaced quickly and conveniently without requiring opening or disassembling of the turbidimeter.

It is a further object of this invention to provide a turbidimeter that significantly reduces the problem of cuvette fogging and the erroneous measurements that result therefrom.

It is a further object of this invention to provide a turbidimeter that efficiently utilizes a single analyzer to perform both turbidity and filter backwash measurements, as well as required calibrations of the apparatus.

It is a further object of this invention to provide a turbidimeter that utilizes an improved display, which provides both instantaneous measurements and an accurate record of turbidity and/or backwash transmittance over time.

It is a further object of this invention to provide a turbidimeter that is internally calibrated without requiring opening or disassembly of the apparatus sensor.

This invention features a turbidimeter including a sensor apparatus that has a housing with first and second receptacles. There are means for establishing an incident light beam within the housing. Such means for establishing include a light source module that is releasably engaged with the first receptacle. A test liquid holder is removably received by the second receptacle for positioning a liquid to be tested in the path of the incident light beam. Means are disposed in the housing at an angle to the incident light beam for sensing light scattered by the test liquid. Means, responsive to the means for sensing, are provided for generating a signal that is representative of the amount of light scattered by the test liquid. An analyzer apparatus includes means, responsive to the means for sensing, for determining the turbidity of the test liquid. Means, responsive to the means for determining, are provided for indicating the turbidity of the test liquid.

In a preferred embodiment, means are provided for temporarily locking the light source module to the housing. Means may also be provided for temporarily locking the holder to the housing. The holder may include a substantially transparent container having inlet and outlet ports formed therein for introducing test liquid into and removing test liquid from the container.

Means may also be provided for drying the outside surface of the container. Such means for drying may include means for circulating air about the container. The means for drying may further include desiccant means for removing moisture from the air that circulates about the container. Means may also be provided for heating the air that circulates about the container.

An optical block may be mounted within the housing in communication with the first and second receptacles for directing the incident light beam through the holder. Port means are typically formed through at least the bottom of the optical block. The side of the optical block may further include port means for circulating the drying air therethrough. Drain means are preferably formed in the housing to prevent catastrophic damage in the case of a ruptured cuvette and float valve means are utilized for normally closing the drain means. The float valve means are raised by liquid that leaks from the holder, in case of cuvette rupture, through the port means in the bottom of the optical block to allow water that has leaked to be discharged through the drain means.

The means for indicating may further include alarm means for signalling when the turbidity of the test sample deviates from a predetermined range. The means for indicating may include both a graphic display for reflecting a series of turbidity measurements over time and an instantaneous numeric display of turbidity time, date and alarm settings. The graphic display may include a high turbidity reading, a low turbidity reading and an average turbidity reading at each of the series of measurements.

This invention may further include a backwash sensor having means for directing a second incident beam of light at a backwash test sample. In such cases means are provided for detecting the light transmitted through the backwash sensor. The analyzer may include means, responsive to the means for sensing and the means for detecting, for selectively determining the turbidity of the test liquid and the light transmittance through the backwash test sample. The analyzer may further include means, responsive to the means for determining, for selectively indicating the turbidity of the test liquid and the percentage of light transmittance through the backwash test sample.

In cases where the analyzer detects both turbidity and backwash transmittance, the means for indicating may include alarm means for signalling when the light transmittance through the backwash test sample reaches a predetermined level. Such means for indicating may again include a graphic display for reflecting a series of light transmittance measurements and an instantaneous numeric display of light transmittance.

DETAILED DESCRIPTION OF PREFERRED EMBODIMENTS

Other objects, features and advantages will occur from the following description of a preferred embodiment and the accompanying drawings in which.

Figure 1:
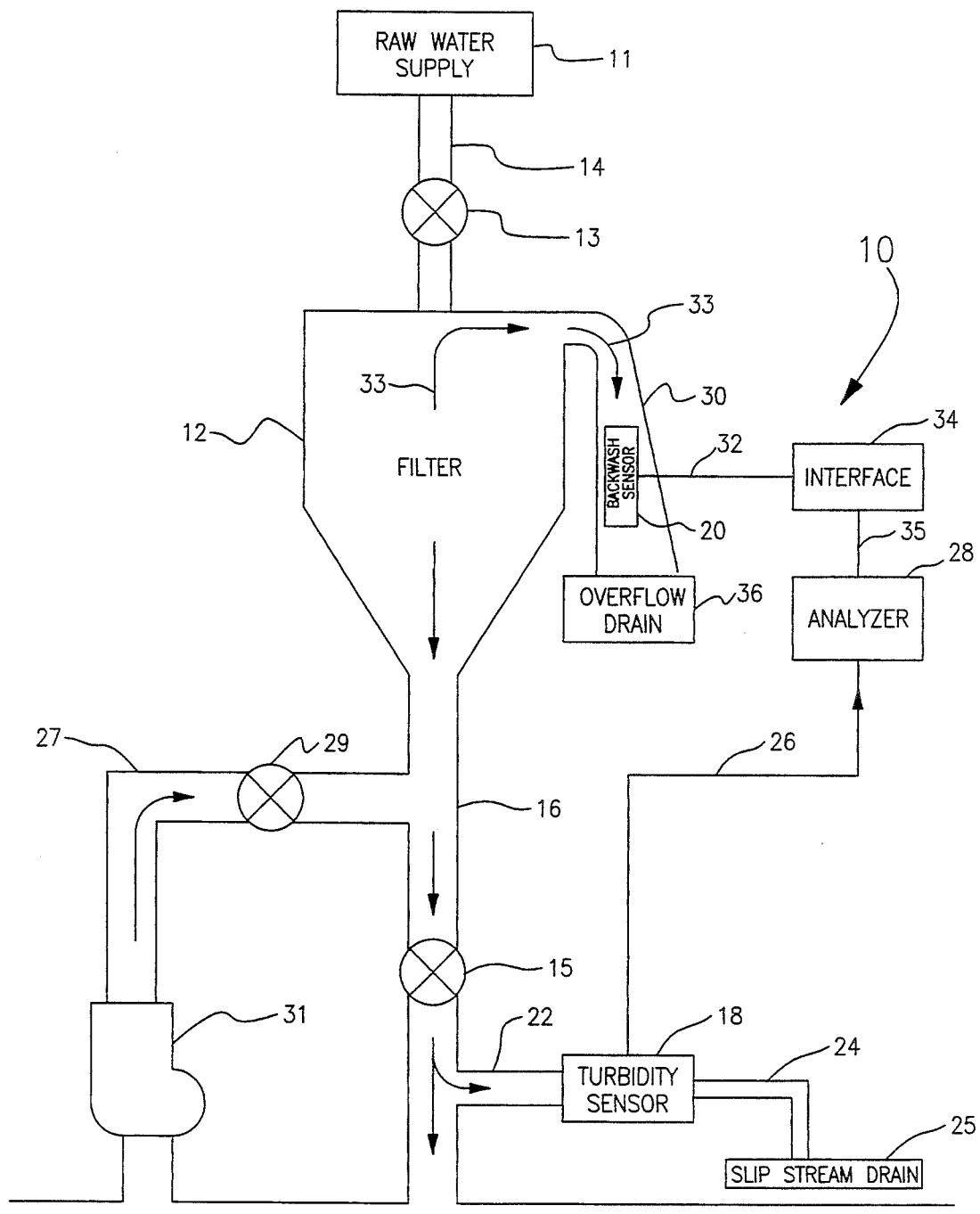
FIG. 1 is a diagrammatic view illustrating the components of the turbidimeter of this system operably engaged with a water filtration system.

There is shown in FIG. 1 a turbidimeter 10 that is operably connected to a water filtration system. A water supply 11 is connected to a conventional filter 12 by an upstream water line 14. A valve 13 in line 14 is opened to deliver water from supply 11 to filter 12. Filter 12 delivers filtered water through a downstream line 16 and an open valve 15 to a customer service line 17. The valves may comprise conventional valves employed in the water purification industry.

Turbidimeter 10 includes a turbidity sensor 18 that is operably engaged with downstream line 16 and a backwash sensor 20 that is mounted in a known manner in the overflow spillway 30 of filter 12. During normal operation filtered water is introduced through a slip stream line 22 into sensor 18. The sensor detects the light scattered by particulate matter in this water and provides a representative signal over line 26 to an analyzer 28. The analyzer then utilizes an appropriate signal processor and software to compute and display the linearized turbidity of the filtered water. The tested water is discharged from sensor 18 through an outlet 24 to a slip stream drain 25.

A backwash line 27 interconnects lines 16 and 17. A backwash valve 29 is disposed in line 27 and a pump 31 is employed for selectively delivering water from line 17 to backwash filter 12. The light transmittance of the backwash effluent is tested in the following manner. Valves 13 and 15 are closed. Valve 29, which remains closed during normal operation, is opened and filtered water is directed by pump 31 through line 27 and into filter 12. This water rises in the filter and eventually flows, in the direction of arrows 33, into overflow spillway 30. Therein the backwash effluent flows past sensor 20 and to overflow drain 36. Sensor 20 comprises a conventional backwash sensor, which will be known to those skilled in the art. In particular, the backwash sensor includes a light source and a detector. Sensor 20 collects backwash effluent from the spillway and light is directed through that effluent. The percentage of light transmitted through the effluent is sensed by the detector in sensor 20. As a result, an analog output signal is directed through line 32 to a backwash interface 34, which converts the analog signal to a frequency modulated signal. The analyzer 28 receives this signal over line 35 and computes and displays backwash transmittance as described more fully below.

Figure 2:
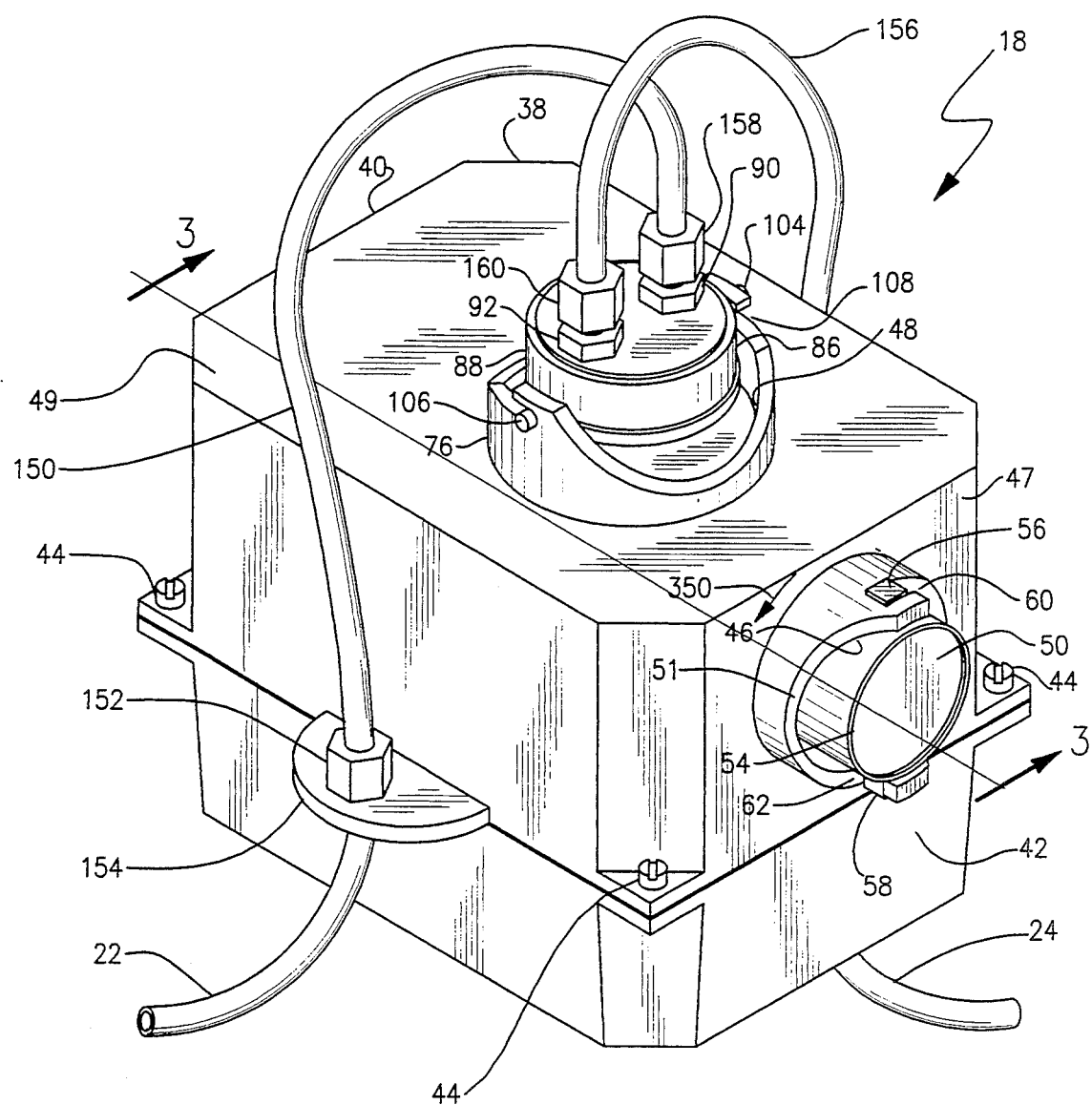
FIG. 2 is a perspective view of the sensor apparatus employed in the turbidimeter.
Figure 2B:
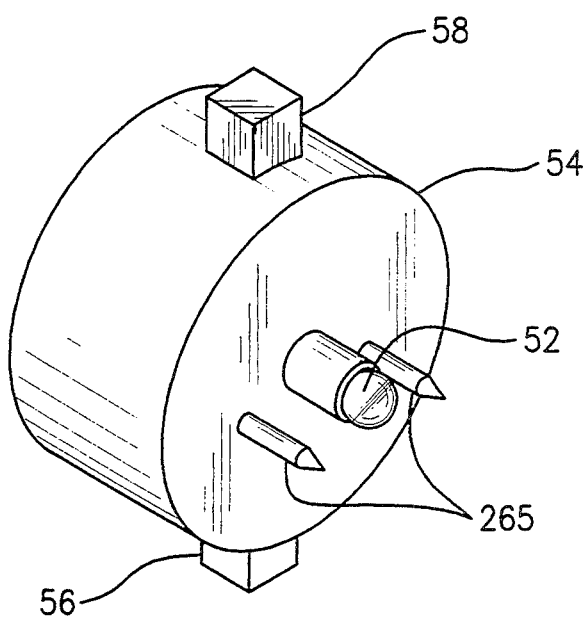
FIG. 2B is a perspective view of the light module.
Figure 2A:
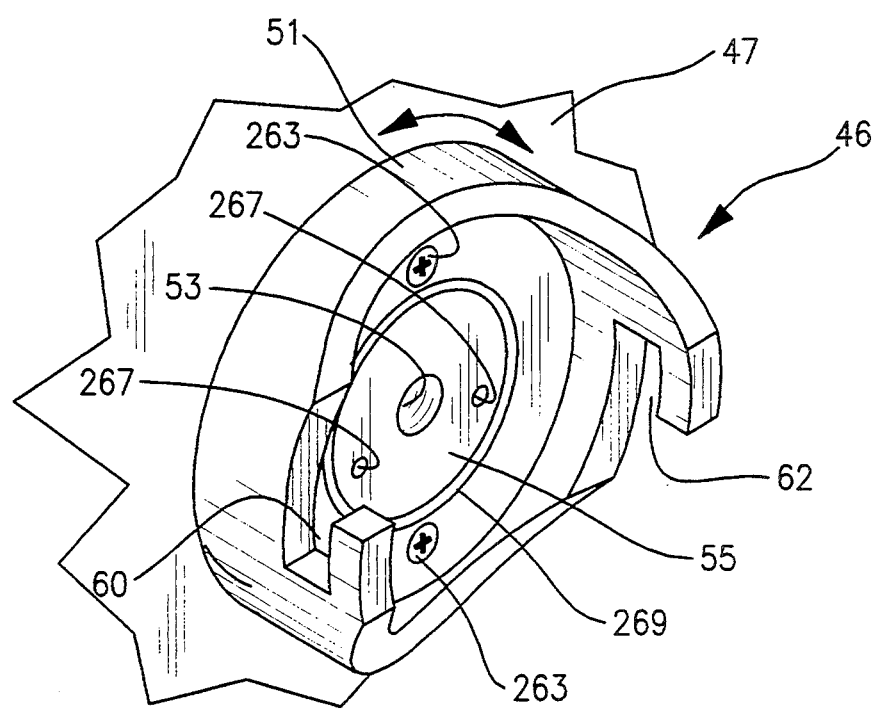
FIG. 2A is a perspective view of the light module receptacle.
Figure 3:
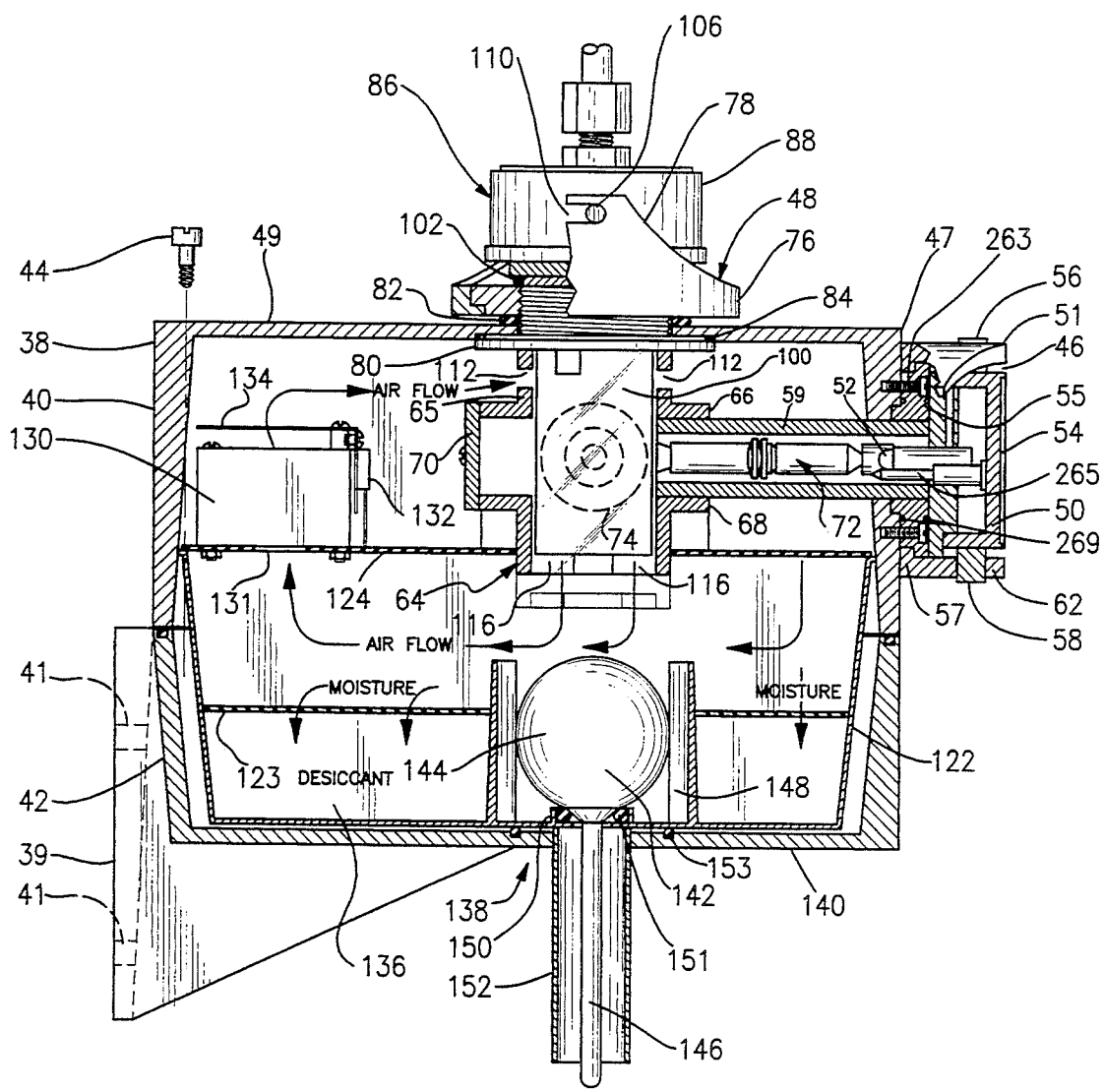
FIG. 3 is a cross sectional view taken along line 3—3 of FIG. 2.

Sensor apparatus 18 is depicted in greater detail in FIGS. 2, and 3. The sensor features a housing 38 having upper and lower halves 40 and 42 that are secured together by a plurality of screws 44 located at the corners of the housing. A bracket 39 attached integrally to lower half 42 has openings 41 for receiving screws or bolts. This permits sensor 18 to be mounted to a wall or other structure. A first receptacle 46, shown alone in FIG. 2A, is formed in the generally vertical forward wall 47 of housing 38. A second receptacle 48 is formed in the generally horizontal upper wall 49.

Receptacle 46 is defined by a locking ring 51 that surrounds an opening 53 in the housing wall 47. The locking ring is swivelably mounted to housing 38 by means of a locking ring retainer 55 (FIG. 3) that is itself secured to the housing by screws 263 (FIGS. 2A and 3). Ring 51 includes a flange 57 that is slidably received in a complementary recess in retainer 55 such that the locking ring rotates about the opening. A tube 59 is mounted within the housing to extend into the retainer 55. Tube 59 carries the optical elements of the sensor, as described more fully below. A light source module 50, shown alone in FIG. 2B, releasably engages receptacle 46. More specifically, module 50 includes a krypton bulb 52 or some other lamp source that is suitable for use in nephelometric monitoring. Bulb 52 is mounted in a typically plastic holder 54 that releasably fits within receptacle 46 such that the bulb extends through the opening 53 and into tube 59. A pair of connector pins 265, FIGS. 2B and 3, are carried by module 50. These pins are received by respective receptacles 267, FIG. 2A, formed through retainer 55. Receptacles 267 are electrically connected to the sensor's power supply such that module 50 is activated when pins 265 are inserted into the receptacles. An O-ring seal 269, FIGS. 2A and 3, is formed on each side of retainer 55 to encircle receptacles 267 and opening 53. As a result, the retainer sealably engages both housing 38 and module 50 when the module is inserted.

A pair of radial connector pins 56 and 58 are also secured to holder 54. To lock module 50 into receptacle 46, the holder 54 and bulb 52 are inserted into receptacle 46, as shown in FIGS. 2 and 3 such that electrical connector pins 265 are plugged into receptacles 267. Locking ring 51 is then rotated in a clockwise direction until pins 56 and 58 are received by slots 60 and 62, respectively, in the locking ring.

As best shown in FIG. 3, a light block 64 is mounted within housing 38 to extend downwardly from top wall 49. Block 64 includes a generally vertical passageway 65 and a horizontal passageway 66 that extends transversely through vertical passageway 65. More particularly, horizontal passageway 66 includes an entry 68 at one end and an opposite closed end 70. A plurality of ports 112 (only two of which are shown) are formed in the side of passageway 65. A second group of ports 116 are formed in the bottom end of passageway 65. Optical elements 72, which may include lenses and other appropriate optical elements known in the nephelometric art, are interengaged in tube 59 between entry 68 of block 64 and light source module 50 in a conventional manner. As a result, light from bulb 52 is directed by optical elements 72 into passageway 66 of block 64 and across the vertical passageway 65 of the optical block. A pair of sensor elements 74, only one of which is shown in FIG. 3, are disposed on opposite sides of passageway 65 at approximately 90° angles to the passageway 66. These sensor elements may comprise various types of conventional photodetectors known to those skilled in the art.

Receptacle 48 communicates with passageway 65 of block 64. In particular, the receptacle 48 is defined by a yoke element 76 that is swivelably mounted to top wall 49 of housing 38. The yoke element operates somewhat analogously to the locking ring of receptacle 46. As best shown in FIG. 3, yoke 76 includes an upper portion 78 that is above wall 49 and a lower flange 80 that is within housing 38. Appropriate O-ring seals 82 and 84 are disposed respectively between the yoke and the housing above and below upper wall 49.

Figure 4:
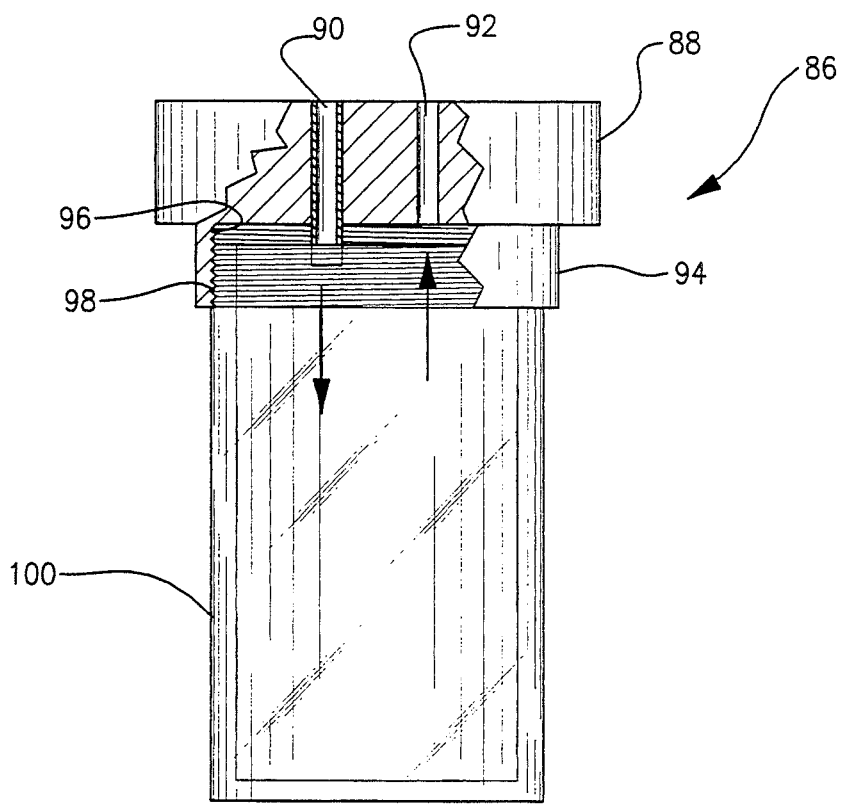
FIG. 4 is an elevational side view of the test liquid holder.

Receptacle 48 communicates with passageway 65 of block 64 to receive a test liquid holder 86. Holder 86, shown alone in FIG. 4, includes a cap 88 through which an inlet 90 and an outlet 92 are formed. Cap 88 includes a reduced diameter portion 94 that has internal threads 96. These threads operably engage the complementary threads 98 of a transparent glass cuvette 100. When the cap and cuvette are so engaged, the inlet 90 and outlet 92 communicate with the interior of cuvette 100.

Holder 86 is received by receptacle 48 in the manner shown in FIGS. 2 and 3. Cuvette 100 depends from cap 88 and extends through passageway 65 of block 64. A small clearance is provided between the outer wall of the cuvette and the inner wall of the optical block. The larger diameter portion of cap 88 extends above receptacle 48. An O-ring seal 102 is disposed between reduced portion 94 and an upper ledge in the yoke 76. Cap 88 carries a pair of diametrically opposed pins 104 (FIG. 2) and 106 (FIGS. 2 and 3). When the holder 86 is engaged with receptacle 48 in the manner described above, cap 88 and yoke 76 may be rotated relative to one another such that pins 104 and 106 are received in respective slots 108 (FIG. 2) and 110 (FIG. 3) in yoke 76. This locks the holder 86 in place within receptacle 48 so that the turbidity of a liquid within cuvette 100 can be tested.

The remainder of the sensor is constructed as follows. A tray 122 sits within the lower half 42 of housing 38. The sides of tray 122 extend upwardly into the upper portion 40 of the housing. Tray 122 contains a desiccant beneath a screen 123. A printed circuit board 124 is seated above tray 122. Printed circuit board 124 carries the electronic components that drive sensor apparatus 18. These components are conventional and readily understood by those skilled in the art. The electronics are connected to a power supply, shown in FIG. 5, which powers the components of sensor 18 as well as those of the analyzer. A fan 130 is mounted on circuit board 124 by appropriate screws and nuts. A voltage regulator 132 is likewise mounted to board 124 adjacent fan 130. A heat sink 134 extends from voltage regulator 132 above the outlet of the fan 130.

Tray 122 is filled to a height of approximately 1" with silica gel 136 or another suitable desiccant. A drain assembly 138 is formed through tray 122 and the bottom 140 of housing 38. In particular, drain assembly 138 includes a float valve 142 having a buoyant ball portion 144 and a stem portion 146. Buoyant ball portion 144 is received in a sump 148 such that ball portion 144 normally engages valve seat 150. The valve seat comprises an opening in the bottom of sump 148 and an O-ring seal 151 that extends about that opening. A discharge tube 152 extends downwardly from valve seat 150 and communicates with upper drain portion 148. The stem 146 of valve 142 extends through tubular section 152. An O-ring seal 153 is formed about tubular section 152 between tray 122 and the inside floor of lower housing section 42.

As shown in FIG. 2, line 22 is connected by a inlet hose 150 to the inlet port 90 through cap 88. More particularly, line 22 and hose 150 are interengaged through ear 154 of housing section 42 by respective fittings 152. Only the upper fitting 152 is shown in FIG. 2. A similar fitting is provided at the end of line 22 below ear 154. Outlet line 24 is connected to the outlet port 92 of holder 86 in an analogous manner by an outlet hose 156. Hose fittings 158 and 160 interconnect hoses 150 and 156, respectively, to the inlet and outlet ports of the holder. The above interconnections permit filtered water to be introduced through line 22 and into the holder 38 so that such water can be monitored by the sensor for turbidity in accordance with this invention. Subsequently, the tested water is discharged through hose 156 and line 24.

The sensor 18 operates in the following manner. Water to be tested is delivered through line 22, hose 150 and inlet port 90 into cuvette 100, which is positioned in passageway 65 of optical 64. An incident beam of light from bulb 52 of lamp module 50 is directed through entry 68 of block 64 and through the liquid test sample in cuvette 100. Detectors 74, disposed at right angles to the incident beam, then measure the degree to which light from the incident beam is scattered by the particles in the sample. This signal is then provided to the analyzer where it is processed and displayed as a turbidity reading in the manner described more fully below.

Fan 130 circulates air continuously about cuvette 100 so that condensation is prevented from building up on the surface of the cuvette. As shown in FIG. 3, the fan operates so that air is circulated through the optical block and along the sides of the cuvette. In particular, the fan includes an inlet 131 that draws air out of the ports 116 of block 64. This air is drawn over desiccant 136, which removes moisture from the air. The fan then draws in the air and discharges it in the direction of arrow 133 such that the air passes over the heat sink 134 that is heated by voltage regulator 132. As a result, the circulating air is heated and dried to an even greater degree. It is then pulled through ports 112 into the passageway 65 of block 64. The heated, dried air is drawn downwardly along the sides of cuvette 100 to remove condensation. Finally, the air is drawn out of bottom ports 116 and the cycle is repeated. This constant heating, drying and recirculation of the air in the housing restricts condensation from building up on the cuvette and improved turbidity measurements are achieved. As a result, the detectors 74 have an improved view through the cuvette.

Drain system 138 is provided so that in the event that a cuvette breaks, water will not overflow into the sensor and damage the electronics. If the cuvette ruptures, water collects in sump 148. Eventually, the water causes the buoyant ball valve 142 to rise and separate from the valve seat 150 so that tubular drain stem 152 is opened. As a result, the water from the broken cuvette drains out through the tube 152 and does not build up within the housing 38 or the tray 122. When the broken cuvette is replaced, the water eventually ceases draining from tube 152 and the valve 142 lowers to engage the valve seat 150.

Figure 5:
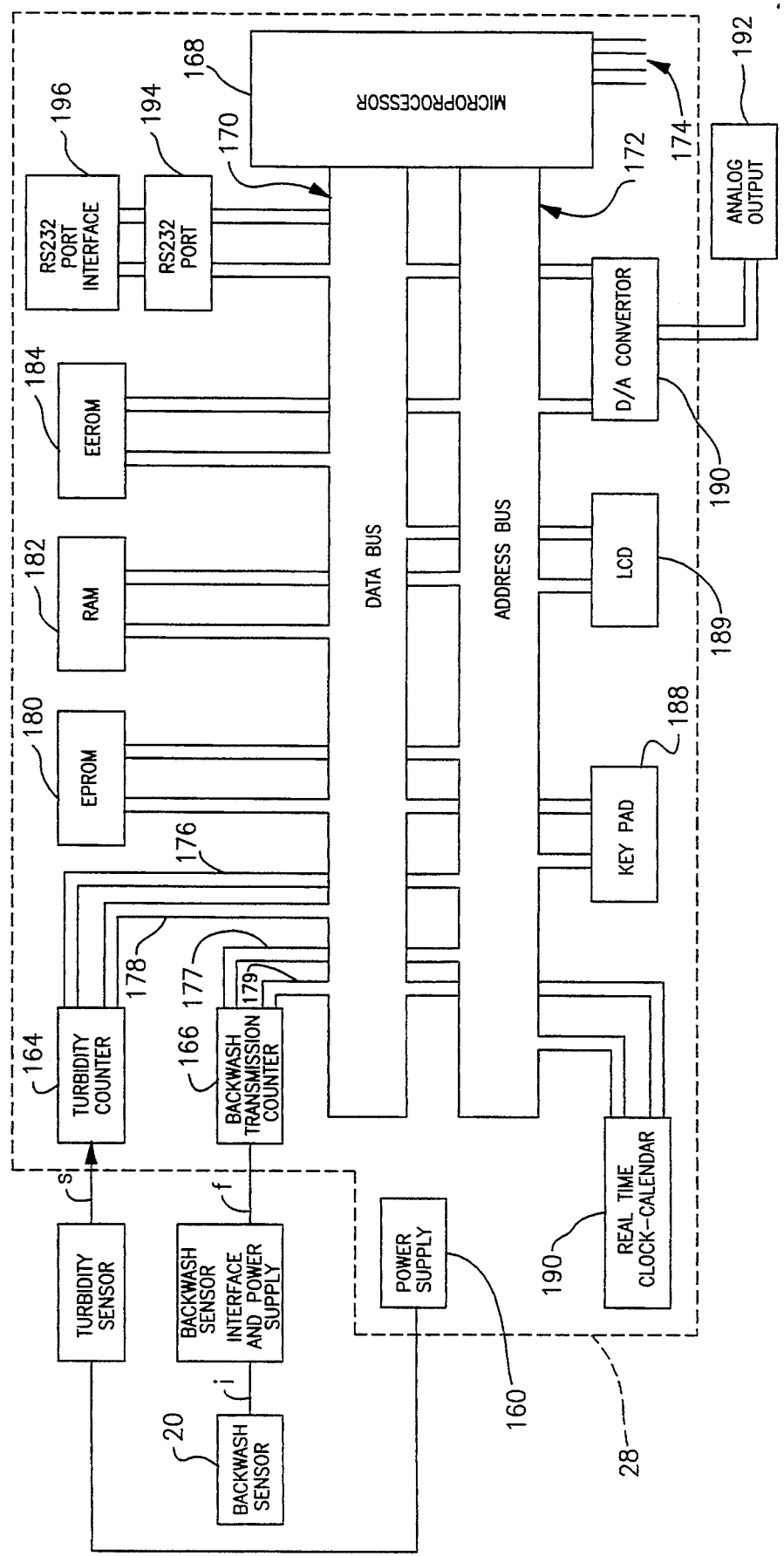
FIG. 5 is a block diagram of the circuitry comprising the turbidimeter.

The signal S generated by sensor 74 is processed in the manner shown in FIG. 5. Turbidity sensor 18 is driven by a power supply 160 within analyzer 28. The power supply is itself connected to an AC outlet in a manner that will be known to those skilled in the art. Power supply 160 provides the direct current voltages for the components of both sensor 18 and analyzer 28. The detectors 74 provide an analog output representative of the degree of scattering of light caused by the water sample. This analog output is converted in sensor 18 to a digital frequency output signal S that is provided to analyzer 28. More particularly, signal S is sent as an input to a turbidity counter 164. Similarly, when backwash is measured, the backwash sensor 20 provides a current signal i to the backwash sensor interface 34, which in turn produces a frequency output signal f that is sent to a second backwash transmission counter 166 in analyzer 28. The backwash sensor is powered by a power supply that is self-contained within the interface 34.

Analyzer 28 includes a microprocessor unit 168 having a data bus 170 and an address bus 172 connected thereto. The microprocessor also includes a plurality of miscellaneous output lines 174 that provide control to different peripheral components of the turbidimeter. Signals are sent to and from the microprocessor over buses 170 and 172 such that turbidity and backwash transmission are calculated and other operations and display functions are performed. In particular, turbidity counter 164 communicates with buses 170 and 172 over lines 176 and 178, respectively. Backwash transmission counter 166 is similarly interconnected to busses 170 and 172 through lines 177 and 179, respectively. These signals from counters 164 and 166 are processed by microprocessor 168 according to an operating program 180. A RAM 182 is provided for storing short term calculations and an EEROM 184 stores functions in a non-volatile form for a long term. The calculated turbidity, or alternatively backwash transmission, are displayed on an LCD display 189 as described more fully below.

A keypad 188 is also connected to buses 170 and 172. The keypad permits various operations to be selected and various settings to be made. For example, the operator may select turbidity measurement, backwash transmission measurement, or one or more calibration modes. The keypad also permits real time clock calendar 190 to be set and called upon for time when required. Alarm parameters for turbidity and backwash transmission may also be entered into the RAM 182 and EEROM 180 through keypad 188. The particular steps involved in programming the analyzer, setting these parameters and entering information into the microprocessor are well understood by those skilled in the art and do not constitute part of this invention. Microprocessor 168 processes the information provided by the turbidity sensor 18 and backwash sensor 20 and determines the turbidity or backwash of the water being tested. That information is then displayed as set forth below.

A D/A converter 190 may to connected to busses 170 and 172. Converter 190 converts the digital output signal from microprocessor 168 to an analog signal that is transmitted through an analog output 192 to a strip chart recorder, graph or other analog display. An RS232 port 194 may be employed to interconnect analyzer 128 to a modem, host computer or other peripheral equipment. Such interconnection is made through an RS232 port interface 196.

Figure 6:
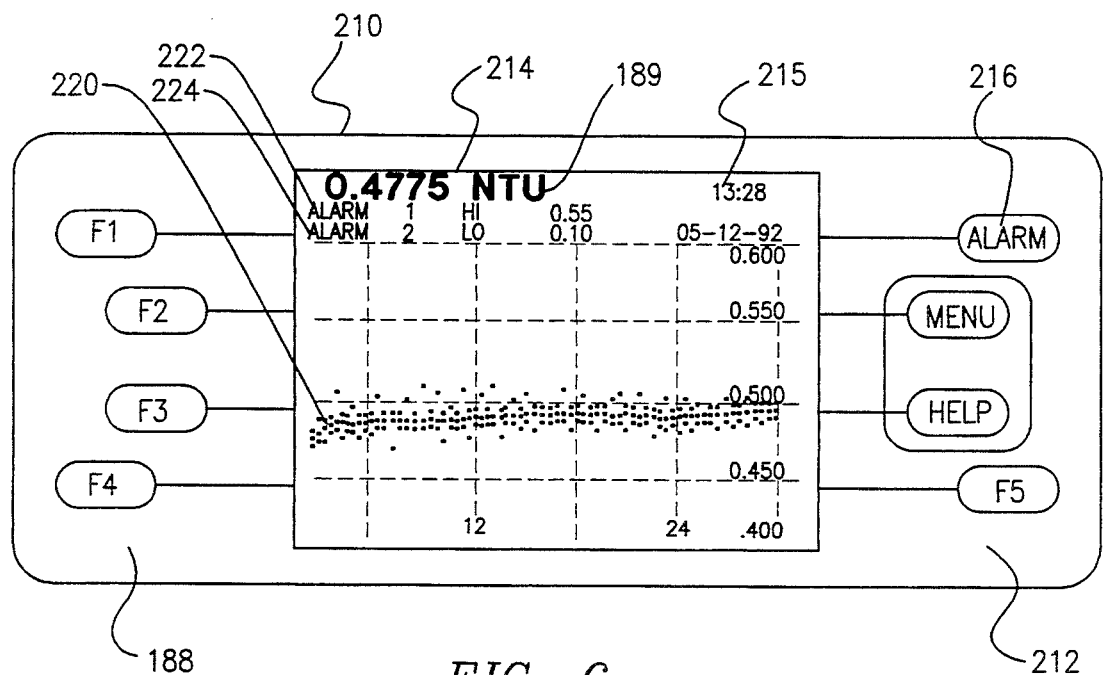
FIG. 6 is an elevational view of a preferred analyzer display in a mode for indicating turbidity.
Figure 7:
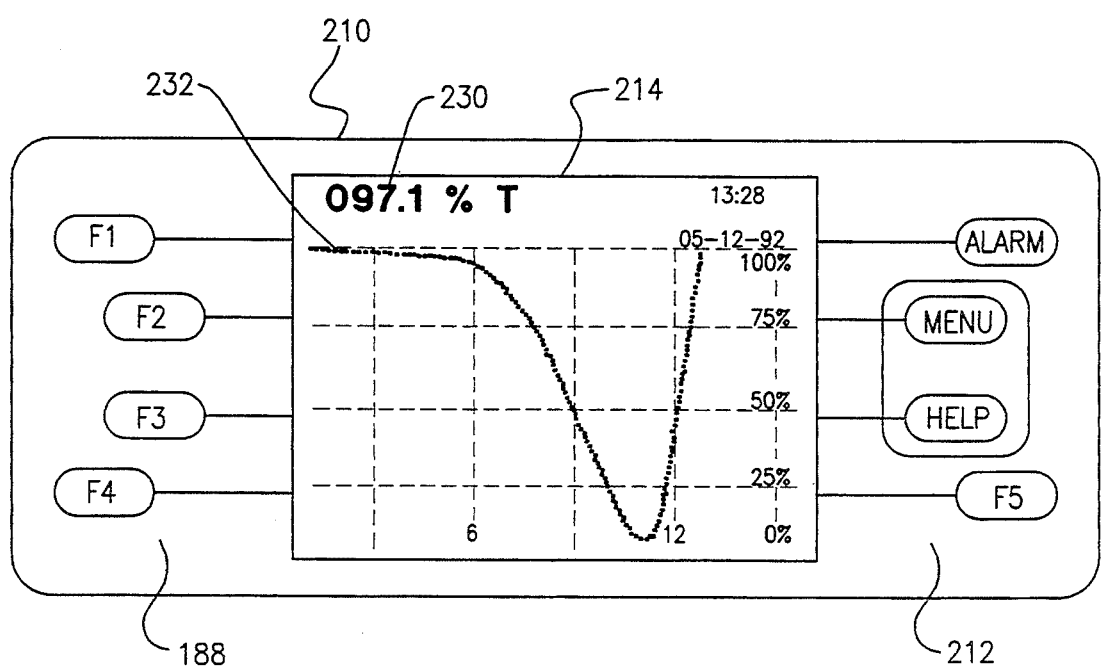
FIG. 7 is a view similar to FIG. 6 of the analyzer display in a mode for indicating the light transmittance of a filter backwash sample.

FIGS. 6 and 7 illustrate a preferred analyzer display panel 210. In FIG. 6 the turbidity is displayed. In FIG. 7 the backwash transmittance is indicated. As described above, the processor 168 may be programmed by suitable software to compute and selectively display the turbidity and backwash transmittance being monitored. Keypad 188 is provided on either side of a screen 214. The key pad operates a menu and permits various screen displays to be selected and functions performed. For example, in addition to monitoring turbidity and backwash, the analyzer can perform calibration of the instrument. Additionally, an alarm key 216 may be pressed to deactivate an alarm programmed to sound if the measurements exceed or drop below desired parameters, e.g. 0.55 and 0.1 NTU.

In FIG. 6 the menu has been accessed and the turbidity mode selected. The upper value "0.4775 NTU" displayed by LCD 189 reflects the measurement of turbidity in nephelometric turbidity units, the standard measure of turbidity. This instantaneous turbidity in LCD form is measured for the time exhibited (13:28 or 1:28 pm) in the upper right of the display at 215. The graphical portion 220 of screen 214 exhibits the turbidity measurements between 0.4 and 0.6 NTU taken over a predetermined period of time. In the disclosed embodiment the desired time period is 24 hrs. Every six minutes the instrument records three pixels on the screen. These three pixels reflect the high, low and average turbidity measurements during that period. As a result, the operator is provided not only with a very accurate history of the turbidity over a 24 hour period but also with the high and low readings specifically noted. Because the average is provided, the high and low readings will not be confused as the actual readings during the time period. Display 214 also employs a high alarm display 222 and a low alarm display 224. If the instantaneous turbidity exceeds 0.55 or drops below 0.10 NTU an audio alarm will sound to warn the operator that an Undesirable turbidity has been sensed.

In FIG. 7, display 214 is in the backwash transmittance mode. This mode is selected by engaging an appropriate one of the keys (typically the menu key) in key pad 212. The upper display reading 230 reflects the percentage of light transmitted through the backwash water at any given instant (e.g. 97.1%). Graphic display 232 reflects the measured transmittance at predetermined time intervals.

Periodically, the lamp module 50 will malfunction and require replacement. This is accomplished by rotating locking ring 51 counterclockwise in the direction of arrow 350, FIG. 2, such that slots 60 and 62 disengage pins 56 and 58, respectively. Module 50 is then pulled straight out from receptacle 46. The procedure is reversed to install a new module.

Figure 8:
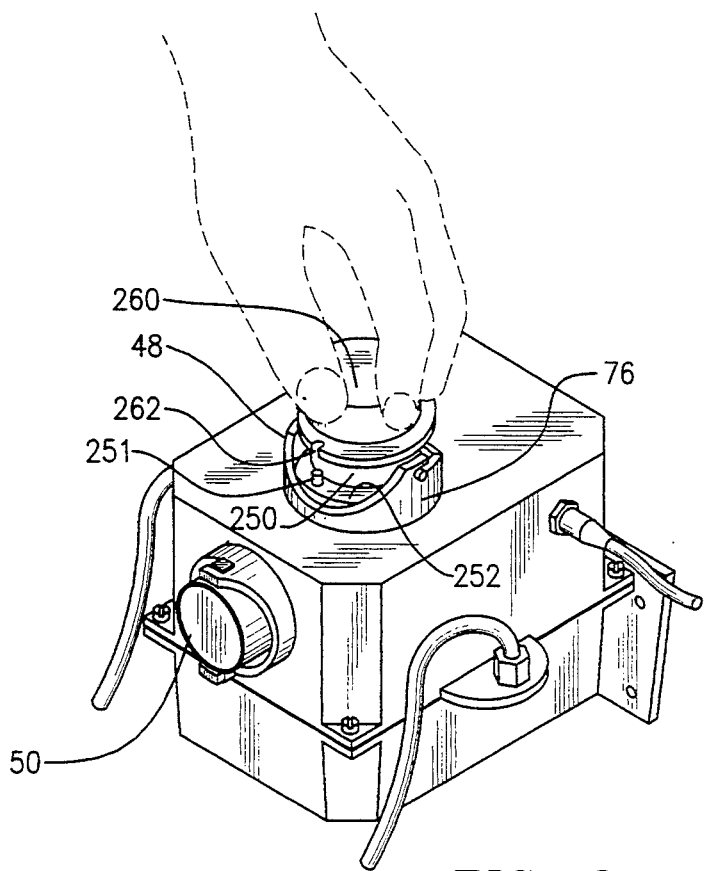
FIG. 8 is a perspective view illustrating how the sensor is standardized.

Before turbidimeter 10 is initially operated or following the replacement of the light source module, the sensor 18 and analyzer 28 should be calibrated. This is accomplished by utilizing appropriate calibration standards. Initially, the standard is indexed in the manner shown in FIG. 8. The holder and attached cuvette are removed from receptacle 48 and a reference standard 250 comprising a pure liquid sealed in glass and having a "turbidity-free" value of 0.02 NTU is introduced into receptacle 48. A locator ring 252 is disposed within yoke 250 about receptacle 48. Ring 252 contains a locator pin 251 that is generally aligned with a lamp module 50. The standard 250 is indexed by placing it within the receptacle and switching the analyzer to the calibration mode. In this mode, various turbidity readings will be provided for the standard. The standard is rotated within the receptacle until the lowest reading of turbidity is provided. A cap 260 is then placed over standard 250 such that a notch 262 in cap 260 is aligned with locator pin 251.

After the standard 250 has been indexed in the above manner, the operator engages a key (e.g. F1) on the analyzer display 210. Appropriate software known to those skilled in the art calibrates the 0.02 NTU reference standard to compensate for aging of the light source, dust on the detector or other physical changes. The sensor may then be calibrated for various respective turbidity ranges (e.g. 0–1 NTU or 0–100 NTU) by introducing a standard full scale Formanzin solution into receptacle 28, selecting the calibration mode from the menu and engaging an appropriate key on the display. Again, the analyzer is programmed in a known manner to perform full scale calibration. An analogous operation can also be performed by the microprocessor to calibrate the sensor to the analyzer. Each time a reference standard is introduced for calibration it should be indexed in the manner described above.

Subsequently, when holder 86 is replaced in receptacle 48, the cuvette should initially be indexed to determine the point where the reading is minimum. This minimizes the effect of glassware anomaly on the turbidity measurement. This is done by switching the analyzer to the turbidity testing mode. When the cuvette is initially received in the receptacle it should be rotated until the lowest turbidity reading is achieved and reflected on the display. Yoke 76, FIGS. 2 and 3, is then rotated so that its slots 108 and 110 engage with the pins 104 and 106 of holder 86. While this is being done, the inlet and outlet hoses 150 and 156 are secured closed by appropriate clamps. When the lowest reading possible is achieved, the yoke is locked onto the holder and the clamps are released. Water passes through the flow-through cuvette 100 and readings may be taken in the above described manner.

Alternatively, individual "grab samples" may be tested by turbidimeter 10. This is accomplished by removing holder 86 and introducing into receptacle 48 an individual cuvette containing the sample to be tested. The test is otherwise performed in the manner described above.

Although specific features of the invention are shown in some drawings and not in others, this is for convenience only, as each of the features may be combined with any or all of the other features in accordance with the invention.

Other embodiments will occur to those skilled in the art and are within the following claims:

What is claimed is:

1. A turbidimeter comprising:
   a sensor apparatus that includes a housing having first and second receptacles formed through respective first and second walls of said housing, means for establishing an incident light beam within said housing, said means for establishing including a light source module that is releasably engaged with said first receptacle, said module including a lamp and a lamp holder that extends from said first wall exteriorly of said housing and carries said lamp such that said lamp is located at least partly inside said housing, a test liquid holder removably received by said second receptacle for positioning a liquid to be tested in the path of said incident light beam, and means disposed in said housing for sensing light scattered by said test liquid, and generating a signal representative of the amount of light scattered by said test liquid;
   an optical block separate and distinct from and mounted within said housing and communicating with said first and second receptacles for directing said incident light beam through said holder, said optical block including a first, vertical passageway that communicates with said second receptacle for accommodating said test liquid holder and a second transverse passageway that transmits said incident light beam to said test liquid;
   an electrical power source for energizing said light source module and said means for sensing and generating, said module including means for electrically connecting said lamp with complementary means disposed in said housing, which complementary means are electrically connected to said power source to provide electrical power to said lamp; and
   an analyzer apparatus that includes means, responsive to said generated signal, for determining the turbidity of said test liquid and means, responsive to said means for determining, for indicating the turbidity of said test liquid.

2. The device of claim 1 further including means for temporarily locking said light source module to said housing, which means comprise a plurality of pins carried by said lamp holder and a locking ring rotatably mounted to said first wall of said housing and having slot means for selectively engaging said plurality of pins to lock said module to said housing.

3. The device of claim 1 further including means for temporarily locking said liquid holder to said housing, which means comprise a plurality of pins carried by said liquid holder and a locking ring rotatably mounted to said second wall of said housing and having slot means for selectively engaging said plurality of pins to lock said liquid holder to said housing.

4. The device of claim 3 in which said holder includes a substantially transparent container having inlet and outlet ports formed therein for introducing test liquid into and removing test liquid from said container.

5. The device of claim 1 in which outlet port means are formed through at least a bottom of said optical block.

6. The device of claim 5 in which said optical block further includes inlet port means and further including means for drying the outside of said test liquid holder, said means for drying including means for circulating air through said inlet and outlet port means of said optical block.

7. The device of claim 6 in which said means for drying include desiccant means for removing moisture from the air that circulates about said holder.

8. The device of claim 6 in which said means for drying include means for heating the air that circulates about said holder.

9. The device of claim 1 further including drain means formed in said housing and float valve means for normally closing said drain means, said float valve means being raised by liquid that leaks from said holder through said outlet port means to allow said water to discharge through said drain.

10. The device of claim 1 in which said means for indicating further includes alarm means for indicating when the turbidity of said test sample deviates from a predetermined range.

11. The device of claim 1 in which said means for indicating include both a graphic display for reflecting a series of turbidity measurement over time and an instantaneous numeric display of turbidity.

12. The device of claim 1 in which said means for connecting include electrical connector pins carried by said lamp holder and said complementary means include electrical receptacles mounted in said housing for respectively receiving said electrical connector pins.

13. A turbidimeter comprising:
a sensor apparatus that includes a housing having first and second receptacles formed through respective first and second walls of said housing, means for establishing and incident light beam within said housing, said means for establishing including a light source module that is releasably engaged with said first receptacle, said module including a lamp and a lamp holder that extends from said first wall exteriorly of said housing and carries said lamp such that said lamp is located at least partly inside said housing, a test liquid holder removably received by said second receptacle for positioning a liquid to be tested in the path of said incident light beam, and means disposed in said housing for sensing light scattered by said test liquid, and generating a signal representative of the amount of light scattered by said test liquid;

an optical block separate and distinct from and mounted within said housing and communicating with said first and second receptacles for directing said incident light beam through said holder, said optical block including a first, vertical passageway that communicates with said second receptacle for accommodating said test liquid holder and a second transverse passageway that transmits said incident light beam to said test liquid; and port means formed through at least a bottom of said optical block;

an electrical power source for energizing said light source module and said means for sensing and generating, said module including means for electrically connecting said lamp with complementary means disposed in said housing, which complementary means are electrically connected to said power source to provide electrical power to said lamp;

an analyzer apparatus that includes means, responsive to said generated signal, for determining the turbidity of said test liquid and means, responsive to said means for determining, for indicating the turbidity of said test liquid; and drain means formed in said housing and a float valve means for normally closing said drain means, said float valve means being raised by liquid that leaks form said holder through said port means to allow said water to discharge through said drain means.

14. A turbidimeter comprising:
a sensor apparatus that includes an exterior housing having first and second receptacles formed through respective first and second walls of said housing, means for establishing an incident light beam within said housing, said means for establishing including a light source module that is releasably engaged with said first receptacle, said module including a lamp and a lamp holder that extends from said first wall exteriorly of said housing and carries said lamp such that said lamp is located at least partly inside said housing, a test liquid holder removably received by said second receptacle for positioning a liquid to be tested in the path of said incident light beams, and means disposed in said housing for sensing light scattered by said test liquid, and generating a signal representative of the amount of light scattered by said test liquid;

an optical block separate and distinct from and mounted within said housing and communicating with said first and second receptacles for directing said incident light beam through said holder, said optical block including a first, vertical passageway that communicates with said second receptacle for accommodating said test liquid holder and a second transverse passageway that transmits said incident light beam to said test liquid;

an electrical power source for energizing said light source module and said means for sensing and generating, said module including means for electrically connecting said lamp with complementary means disposed in said housing, which complementary means are electrically connected to said power source to provide electrical power to said lamp;

a backwash sensor having means for directing a second incident light beam at a backwash test sample and means for detecting the light transmitted through said backwash test sample and generating a signal representative of said light transmittance; and an analyzer apparatus including means responsive to said means for sensing and generating and said means for detecting and generating for selectively determining the turbidity of said test liquid and the transmittance of light through said backwash test sample, and means, responsive to said means for determining for selectively indicating the turbidity of said test liquid and the percentage of light transmittance through said backwash test sample.

15. The device of claim 14 in which said means for indicating include alarm means for indicating when the light transmittance through said backwash test sample deviates from a predetermined range.

16. The device of claim 14 in which said mean for indicating includes both a graphic display for reflecting a series of light transmittance measurements over time and an instantaneous numeric display of light transmittance through said backwash test sample.

* * * * *